United States Patent [19]
Steinberg et al.

[11] Patent Number: 6,060,046
[45] Date of Patent: May 9, 2000

[54] ANTIFOULING COMPOSITIONS

[75] Inventors: Peter D. Steinberg, Newtown; Peter C. De Nys, Bronte, both of Australia

[73] Assignee: Unisearch Limited, New South Wales, Australia

[21] Appl. No.: 08/765,226

[22] PCT Filed: Jul. 5, 1995

[86] PCT No.: PCT/AU95/00407

§ 371 Date: Feb. 27, 1997

§ 102(e) Date: Feb. 27, 1997

[87] PCT Pub. No.: WO96/01294

PCT Pub. Date: Jan. 18, 1996

[30] Foreign Application Priority Data

Jul. 6, 1994 [AU] Australia ................ PM6666

[51] Int. Cl.$^7$ .............. A61K 31/365; C07D 307/33
[52] U.S. Cl. ............ 424/78.09; 549/295; 549/313; 549/315; 549/318
[58] Field of Search ............ 424/78.09; 106/18; 523/122; 549/315, 313, 318, 295

[56] References Cited

U.S. PATENT DOCUMENTS

| | | | |
|---|---|---|---|
| 5,248,221 | 9/1993 | Gerhart et al. | 405/216 |
| 5,266,359 | 11/1993 | Spielvogel | 427/388.4 |

FOREIGN PATENT DOCUMENTS

| | | | |
|---|---|---|---|
| A 54043/94 | 5/1994 | Australia . | |
| 1 497 064 | 1/1978 | United Kingdom . | |

OTHER PUBLICATIONS

Derwent Abstract Accession No. 95–110609/15, Class C02, JP, 07–033741, Mar. 2, 1995.

de Nys, R. et al.: New halogenated furanones from the marine alga *Delisea pulchra* (cf. *fimbriata*), Tetrahedron, vol. 49, pp. 11213–11220, 1993.

de Nys, R. et al.: *Delsea pulchra* (cf. *fimbriata*) revisited. The structural determination of two new metabolites from the red sea *Delisea pulchra*. Aust. J. Chem. vol. 45, pp. 1625–1632, 1992.

Pettus, J.A. et al.: Marine natural products XII isolation of a family of multihalogenated gamma–methylene lactones from the red seaweed *Delisea fimbriata*. Tetrahed. Lett. vol. 1, pp. 41–44, 1977.

Kazlawskas, R. et al.: A New Class of Halogenated Lactones from the Red Alga *Delisea fimbriata* (BonnemaiSoniaceae). Tetrahedron Letters. No. 1, pp. 37–40, 1977.

*Primary Examiner*—Alan L. Rotman
*Assistant Examiner*—Charanjit S. Aulakh
*Attorney, Agent, or Firm*—Nixon & Vanderhye

[57] ABSTRACT

An antifouling composition that comprises an effective amount of a furanone of the structure shown and a suitable carrier therefor. In the figure, substituents $R_1$, $R_2$ and $R_3$ are each a hydrogen atom, a hydroxyl group, an alkyl group containing from 1 to 10 carbon atoms, an ether group containing from 1 to 10 carbon atoms, an ester group containing from 1 to 10 carbon atoms or a halogenated alkene containing from 1 to 10 carbon atoms or $R_2$ and $R_3$ together may comprise an unsubstituted or a halogenated alkene containing from 1 to 10 carbon atoms and $R_4$ is a hydrogen or halogen atom, and a suitable carrier therefor.

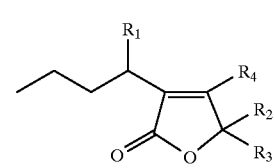

(I)

9 Claims, 7 Drawing Sheets

Fig. 1A

|    | R1  | R2    | R3 |
|----|-----|-------|-----|
| 1  | H   | Br    | Br |
| 2  | H   | H     | Br |
| 3  | OAc | H     | Br |
| 4  | OH  | H     | Br |
| 5  | OAc | H     | I  |
| 9  | H   | CH₂Br | Br |
| 10 | OAc | Br    | Br |

ANTIFOULING COMPOSITIONS

This application is a 371 of PCT/AU 95/00407, filed Jul. 5, 1995, which is now published as WO96/01294 on Jan. 18, 1996.

FIELD OF THE INVENTION

The present invention relates to marine antifouling composition containing naturally occurring compounds.

BACKGROUND ART

Biofouling is the settlement and subsequent growth of marine organisms on submerged surfaces. Because these surfaces are in many instances artificial, e.g. boat hulls, oil and gas platforms, aquaculture nets and enclosures, fouling organisms present a significant problem to human activities in the ocean. The formation of fouling communities on boats increases drag; reducing ship speed while increasing fuel costs and dry dock time; fouling of semi-permanent offshore structures increases structural loading and corrosion, and fouling of nets and enclosures adds significant costs to the maintenance of aquaculture systems. The increased fuel usage, drydocking, structural inspection, maintenance etc. resulting from biofouling has been estimated to cost the world's marine industries over $3.5 billion dollars per year.

Fouling is primarily combatted by the use of antifouling coatings which are applied to the surfaces of boats or other marine structures. These coatings rely almost exclusively on heavy metals particularly copper and tin based compounds for their active ingredients. These compounds leach into the water from the coating, killing fouling organisms. Unfortunately, these compounds also kill non-target organisms in the environment at large, and the general environmental effects of these compounds is of worldwide concern. (Dalley 1989). Tin based coatings are particularly toxic, and such coatings are now partially (restricted to vessels >25 m in length in NSW, Europe and parts of the USA) or totally (Japan) banned in the world's waterways. It is generally accepted that the use of tin (specifically tributyl tin) based coatings will be completely banned in most countries within the next 5–10 years.

The demise of heavy-metal based antifouling coatings has prompted the search for more environmentally benign antifoulants, and one of the most promising alternative technologies is the use of naturally occurring antifouling compounds derived from natural metabolites from marine organisms (Holmstrom and Kjelleberg 1994).

Marine organisms such as seaweeds, sponges, etc. are also submerged surfaces, and they must detre fouling of their bodies to avoid increases in drag (and being pulled off the bottom) or being smothered. It is now abundantly clear that one of the ways in which marine organisms defend against fouling is via the production of natural antifoulants. Because these compounds already occur in nature, it is thought that these natural metabolites will be less environmentally damaging that the current heavy-metal based paints. A number of metabolites or extracts from marine organisms with antifouling activities typically tested against barnacle larvae have now been identified (Holmstrom and Kjelleberg 1994, Targett et al. 1983, Standing et al. 1984, Rittschof et al., 1985, Gerhardt et al. 1988, Keifer et al. 1986, Sr Mary et al. 1993, Maki et al. 1989, Holmstrom et al. 1992, Todd et al. 1993).

DISCLOSURE OF THE INVENTION

The present invention is directed to alternatives to the heavy metal antifouling compounds. The inventors have found that a group of compounds produced by the Australian red seaweed *Delisea nulchra* may be used as the active ingredients in antifouling contains and related antifouling technologies. These compounds are extremely active against representatives of the three major groups of fouling organisms ie. seaweeds, invertebrates, and bacteria. Moreover, the metabolites are small, stable, and can be synthesized. Their variation in polarity and other chemical features also means that the potential for manipulation and incorporation into a range of polymer coatings is high.

The present invention consists in an antifouling composition comprising an effective amount of a furanone of the structure wherein $R_1$, $R_2$ and $R_3$ are each selected from the group comprising a hydrogen atom, a hydroxyl group, an alkyl group containing from 1 to 10 carbon atoms, an ester group containing from 1 to 10 carbon atoms or a halogenated alkene containing from 1 to 10 carbon atoms or $R_2$ and $R_3$ together may comprise an unsubstituted or a halogenated alkene containing from 1 to 10 carbon atoms, and $R_4$ is a hydrogen or a halogen atom, and a suitable carrier therefore. In another aspect, the present invention relates to a process for the prevention of marine fouling of an object comprising applying to at least a part of the object a coating of the composition according to the present invention or incorporating in the object itself such a composition, and immersing at least that part of the object into water.

The compounds to which the present invention relates consist of a series of structurally related halogenated furanones. The compounds have been previously described in the literature, (Kazlauskas et al., 1977; de Nys et al., 1992; de Nys et al., 1993), where their molecular structures have been elucidated and characterised by nuclear magnetic spectroscopy, mass spectrometry, ultra-violet and infra-red spectroscopy and optical rotation (αD). The structures have been fully characterised (de Nys et al., 1992; de Nys et al., 1993). The compounds all share a basic carbon skeleton consisting of a furanone moiety with a butyl side chain at the 3-position Substitution occurs at the $R_1$ and $R_2$, $R_3$ positions of the basic structure.

The alkyl group, ether group, ester group and the alkene group preferably have 1 to 5 carbon atoms, most preferably 1 to 3 carbon atoms. The halogen atoms are preferably bromine, chlorine and iodine, most preferably bromine.

The substitution of hydrogen, hydroxy and acetoxy groups at the $R_1$ position, and the substitution of a single unsubstituted or halogenated methylene group for $R_2$ and $R_3$ is preferred and results in a large series or structurally related metabolites of the formula:

wherein $R_1$ is a hydrogen atom, or hydroxyl, ester or an ether group and wherein $R_2$ and $R_3$ are each together and unsubstituted or halogenated methylene group. The combination of the most feasible substitutions at these positions results in 30 possible preferred structures, of which 13 have been characterised. This application is intended to cover, inter alia, all of these 30 preferred compounds.

BRIEF DESCRIPTION OF THE DRAWINGS

The invention will now be described in more detail with reference to the accompanying drawings, in which.

BEST METHOD OF CARRYING OUT THE INVENTION

Figure 1A:
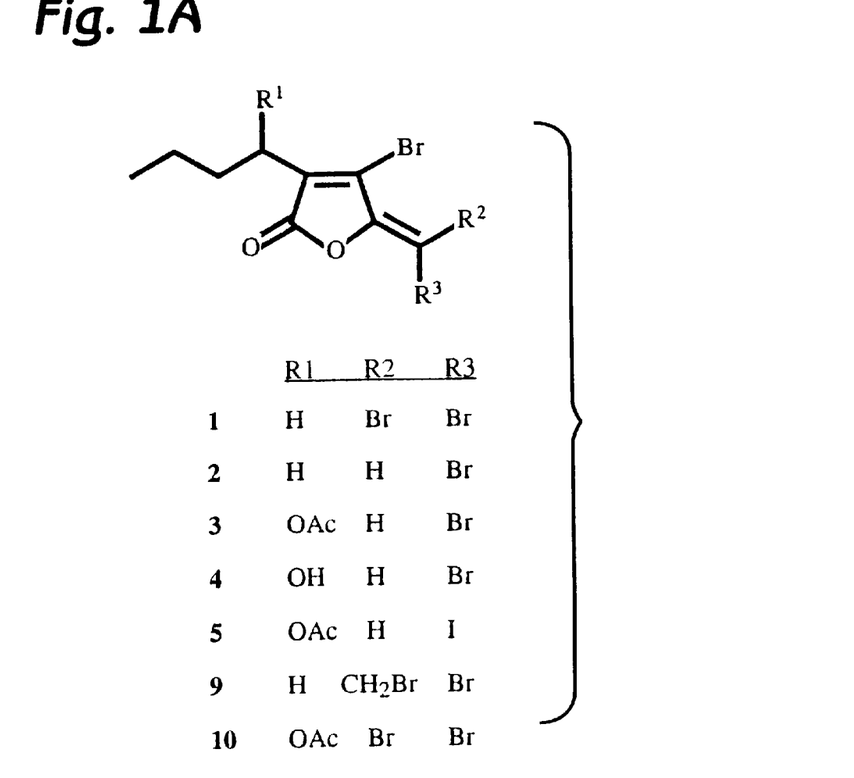
FIGS. 1A–1C show preferred active compounds for use in the present invention (the most preferred being compounds 1 to 6 and 8 to 10)
Figure 1B:
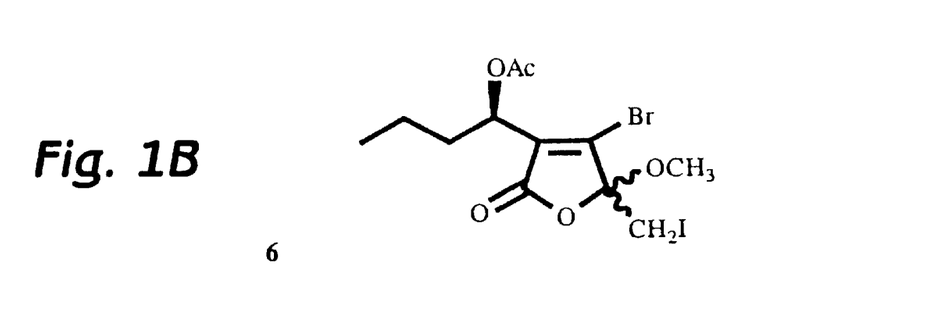
Figure 1C:
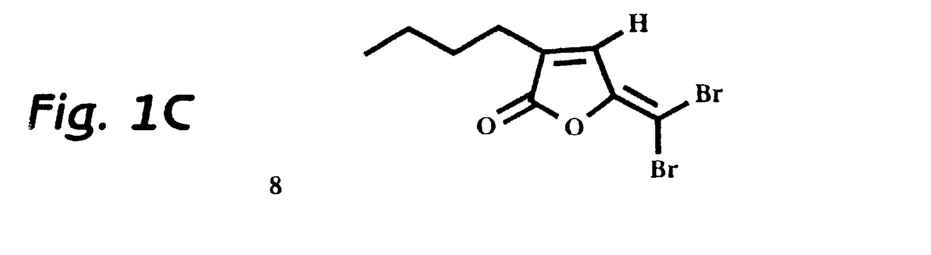

For the antifouling tests described below, *Delisea pulchra* metabolites were extracted as follows: The alga was collected from Cape Banks, NSW, Australia and frozen on collection. The tissue was subsequently freeze dried, extracted with dichloromethane, and the crude extract reduced in vacuo. Purified metabolites were isolated by vacuum liquid chromatography followed by high performance liquid chromatography (de Nys et al., 1993). The structural elucidation of purified metabolites was carried out using a combination of nuclear magnetic resonance spectroscopy and mass-spectrometry techniques. Nine previously characterised Delisea metabolites (FIG. 1 labelled here as compounds 1 to 6 and 8 to 10) were isolated and identified in sufficient quantities for biological testing.

The Delisea metabolites were tested against representatives of four main groups of fouling organisms invertebrates, algae, bryozoan and bacteria. These were barnacle larvae (invertebrates), algal spores, bryozoan larvae and marine bacterial strains. These tests (bioassays) were done in the laboratory under controlled conditions.

Inhibitions of Settlement of Barnacle Cyprid Larvae

Settlement assays were carried out using cyprids of the cosmopolitan fouling barnacle *Balanus amphitrite*. The methods used were similar to those used previously (Rittschof et al, 1994, Willemson 1994). Adult brood stock were maintained under controlled light (15 hr light: 9 hr dark) and temperature (28° C.) conditions and fed larvae of the brine shrimp *Artemia salina* and the diatom *Skeletonema costatum*. Recently spawned nauplii of *B. amphitrite* were collected and reared on *Skeletonema costatum* under the same conditions as adult stocks until reaching cyprid stage after four to five days. Cyprid larvae were subsequently filtered from the culture and maintained in filtered seawater at 5° C. for five days prior to use in settlement assays.

Assays used purified metabolites at concentrations ranging from 100 $\mu$g to 0.1 ng per millilitre. Metabolites 1–5 were dissolved in dimethylsulphoxide (DMSO) (60 $\mu$l/mg-0.6%) prior to being made up to their highest concentration (100 $\mu$l/ml) in 0.45 $\mu$m filtered seawater. Subsequent dilutions were made from these stock solutions. Controls of filtered seawater and the highest concentration of DMSO (0.6%) were run with each experiment. Experiments were repeated using metabolites 2 and 4 using larvae from independent spawning events to determine the reproducibility of results. An experiment comparing all concentration of DMSO used (0.6%–0.6*10–5%) and filtered seawater was also carried out.

Tests were conducted by adding 45–65 cyprids to petri-dishes (47 mm) containing five mls of either test solution, filtered seawater control, or DMSO control. All test solutions and controls were replicated four times. Test dishes were incubated for 24 hours at 28° C. in a 15:9 hr light-dark cycle. Upon completion of incubation non-settled cyprids were observed as swimming or non-swimming and the test was terminated by the addition of three drops of 40% formaldehyde. The dishes were then rinsed and the percent settlement of cyprids was determined by counting settled and non settled larvae.

Antifoulants may work in one of two ways; they may leach out of a coating into the water and inhibit fouling organisms via contact in the water, or they may adhere to a surface and inhibit fouling only via contact of fouling organisms with that surface. The assay described tests the effects of compounds when dissolved in the water. In a second series of assays, the effects of Delisea compounds were tested against barnacle larvae when they were applied to the surface of Petri dishes.

Assays used purified metabolites at concentrations ranging from 500 $\mu$g to 50 ng per millilitre. Metabolites 1–4 were dissolved in ethanol (99.7%+purity) at the highest concentration of 500 $\mu$g/ml. Subsequent dilutions were made from these stock solutions. One ml of each solution was added to a petri dish (surface area 20cm$^2$) and the dish shaken on an orbital shaker until dry. The solvent evaporates and the non-polar metabolites adhere to the plastic petri dish at concentrations ranging from 25$\mu$g/cm$^2$ to 2.5 ng/cm$^2$. Controls of ethanol without added metabolites, and filtered seawater were run with each experiment. All test solutions and controls were replicated three times. The addition of cyprids and subsequent testing of compounds was conducted as for compounds in solution (see above).

Inhibition of Bacterial Growth

Assays to determine the antibacterial effect of Delisea metabolites used the marine isolate SW8 (Neu et al., 1991). This bacterium is relatively resistant to antifoulants and antibiotics due to the presence of a thick polysaccharide envelope attached to the outer cell membrane (Leslie et al., 1993), and hence is a conservative test organism with respect to the effects of potential antifoulants. Purified metabolites 1–4 were dissolved in ethyl acetate (10 mg/ml–10 $\mu$g/ml) and were added in volumes of 20 $\mu$l to sterilised McCartney bottles containing 19 mls of filter sterilised artificial seawater (ASW) medium supplemented with a trace vitamin and mineral solution (Schneider et al., 1994). Two reference compounds for antibacterial activity, the antibiotic gentamicin (Sigma)and a saturated copper (II) oxide solution, were also used in these tests. Following addition of metabolites, antibiotics or copper, the media was inoculated with SW8. The inoculum for the assay was taken from a continuous culture fermenter operating at a cell density of $10^7$ cells/ml. The final concentration of metabolites and antibiotic tested ranged from 10 μg/ml to 10 ng/ml. Control bottles with media only, and media with 20 μl EtOAc added, were inoculated with SW8 and run concurrently with each experiment.

After mixing, 200 μl from each bottle was aseptically transferred to a well in a Nunc Tissue Culture plate (96 well). Plates were incubated aerobically at 30° C. with shaking. Growth was monitored by optical density (600 nm) every hour for 12 hours after which growth was monitored every four hours for a further 18 hours.

The effects of metabolites 1 to 6 and 8to 10 were tested also against the growth of the marine bacterium *Vibric fischeri*. at a concentration of 1 μg/ml. This is an order of magnitude less than the concentration required to inhibit the growth of the marine bacterium SW8.

Inhibition of Settlement and Germination of Algal Spores

Inhibition of settlement and subsequent germination (these two processes were not distinguished in our assays) of algal spores was done using the cosmopolitan fouling alga Ulva. Fertile thalli of Ulva sp., identified by discolouration around the tip of the frond, were collected in the field. The fertile thalli were washed three times in sterile seawater and left to dry for approximately two hours. Once dried, swarmer release was induced by placing the fronds in sterilised seawater. Positively phototactic swarmers were concentrated and identified as either sporophytes or gametophytes by their structural form (Fletcher 1985). While both sporophytes or gametophytes are suitable for the algal assay, gametophytes were used in the assays. Gametophytes were twice "raced" towards a light source across a watchglass containing sterile seawater to remove contaminants and added to 20 ml of sterile seawater prior to use in tests. In order to obtain a uniform suspension for addition to test wells the solution was mechanically stirred.

Purified metabolites 1–4 were dissolved in ethanol (99.7%+purity) at a concentration of 500 μg/ml to 50 ng/ml. 94 μl of test solution was added to repliplate test wells (surface area 1.88 $cm^2$) giving a concentration range of 25 μg/$cm^2$ to 2.5 ng/$cm^2$ for each compound. Control wells containing only ethanol and filtered seawater (0.20 μm) were also prepared. The treatment and ethanol control repli-plate wells were prepared by drying on a shaker. A swarmer suspension (100 μl) was added to cover each well and the repli-plates placed in the dark to allow an even settlement of spores. After 1 hr, 1.5 ml of nutrient enriched sterilised seawater was added to each well and the plates incubated for five days at 28° C. in a 15:9 hr light-dark cycle. After five days the Ulva germlings were counted. Five view fields (3.50 $mm^2$) were counted for each well using an inverted binocular microscope. Numbers of germlings for each well were compared to seawater and ethanol controls.

Inhibition of the Settlement of Bryozoan Larvae

The methodology of this assay has not been previously described. The larvae of the cosmopolitan fouling byrozoan *Bugula neritina* were used for bioassays. Colonies of *E. neritina* were maintained in the laboratory in the dark in aerated filtered sea water at 20° C.±3° C. Larvae were released from the colonies within 10–30 minutes on exposure to a bright light source. These were collected by a pipette and transferred into the petri dishes coated with Delisea metabolite 1–4 (as for barnacle larvae) and containing 4 ml of filtered sea water. Filtered sea water and ethanol controls were used for each assay. Ten larvae were placed in each treatment and control dish and allowed to settle for 24 hours. All the treatments and controls were done in triplicate. The percentage of settlement was determined by counting settled and non-settled larvae.

Statistical Analyses

The effects of *Delisea pulchra* metabolites on the settlement of barnacle cyprid larvae, the growth of bacteria and the settlement and germination of algal spores were analysed in two ways. Firstly, we used Analysis of Variance (ANOVA) followed by Tukey's multiple comparison tests to determine which compounds, at which concentrations, had statistically significant effects on the test organisms. Analyses were done using the Statview II statistical package. These procedures enable us to determine the minimum concentration of a compound necessary to have some significant effect, and to look in a detailed way at variation in the effects of different compounds.

The second analytical procedure used was the determination of the 24 hr-$EC_{50}$ value (the concentration required for 50% settlement inhibition in a 24 hour assay) of Delisea metabolites. This procedure, used in the barnacle assay only, was done using the trimmed Spearmann-Karber method (Hamilton et al. 1977). $Ec_{50}$ values are useful for comparisons to other studies.

RESULTS OF BIOASSAYS

Barnacle Assays

Figure 2:
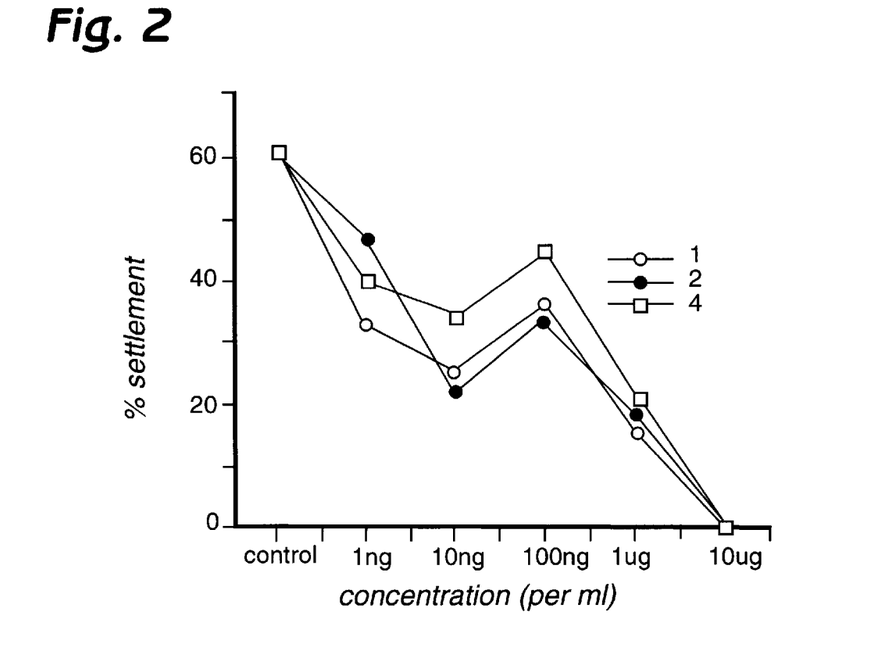
FIG. 2 shows the effects of metabolites dissolved in water in cyprid settlement for compounds 1, 2 and 4.
Figure 4:
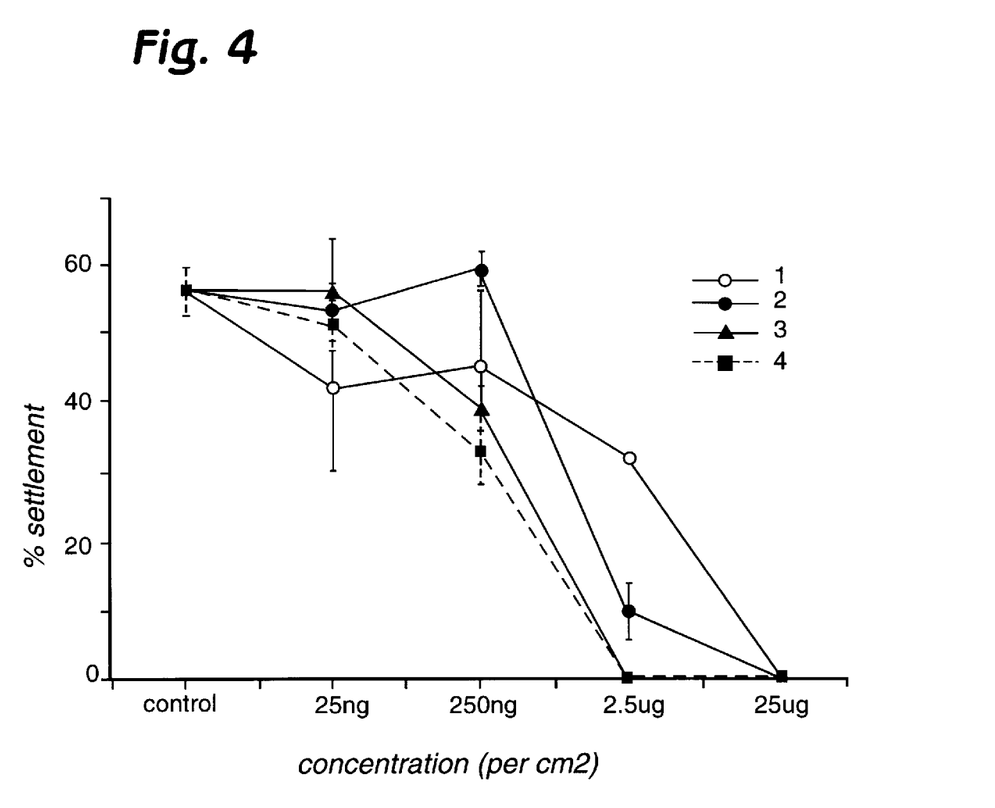
FIG. 4 is a plot of percentage settlement versus concentration demonstrating activity against settlement when applied to the surface of dishes.
Figure 5:
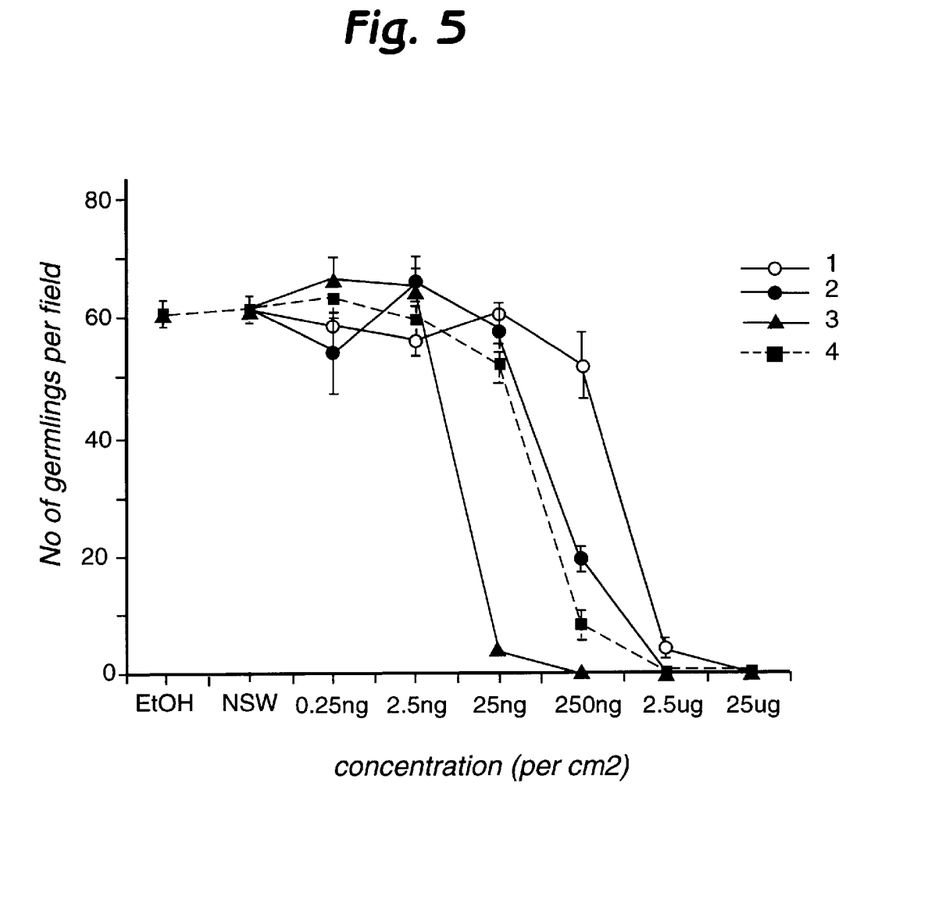
FIG. 5 is a plot of number of germlings per field when processed against concentration showing the effects of surface coalings at metabolites 1–4 coated against the settlement of and germination of algal spores.

The effects of the metabolites dissolved in water in cyprid settlement are shown in FIGS. 2 (for compounds 1, 2 and 4) and 5 (compounds 3, 5,) and Table 1 (statistical results). All 5 compounds showed significant activity against settlement, with activity increasing with increasing concentration. All compounds completely inhibited settlement at a concentration of 10 μg/ml. Three compounds—1, 2 and 2 were particularly inhibitory (FIG. 4, Table 1). All three compounds significantly (Table 1) inhibited settlement at the very low concentrations of 1 and 10 ng/ml. At 10 ng/ml compounds 1 and 2 inhibited settlement by 50%, relative to control settlement levels. Interestingly, these 3 compounds also exhibited non-linear patterns in their effects on settlement. Thus settlement was higher at 100 ng/ml than at 1 or 20 ng/ml for all 3 compounds.

TABLE 1

| concentration | Compounds in order of increasing activity | | | | | |
|---|---|---|---|---|---|---|
| 10 μg/mL | dmso | 5 | | 1 | 2 | 3 | 4 |
| 01 μg/mL | dmso | 5 | | 4 | 2 | 3 | 1 |
| 100 ng/mL | dmso | 4 | | 5 | 3 | 1 | 2 |
| 10 ng/mL | dmso | 5 | 3 | | 4 | 1 | 2 |
| 01 ng/mL | 5 | dmso | | 3 | 2 | 4 | 1 |

Figure 3:
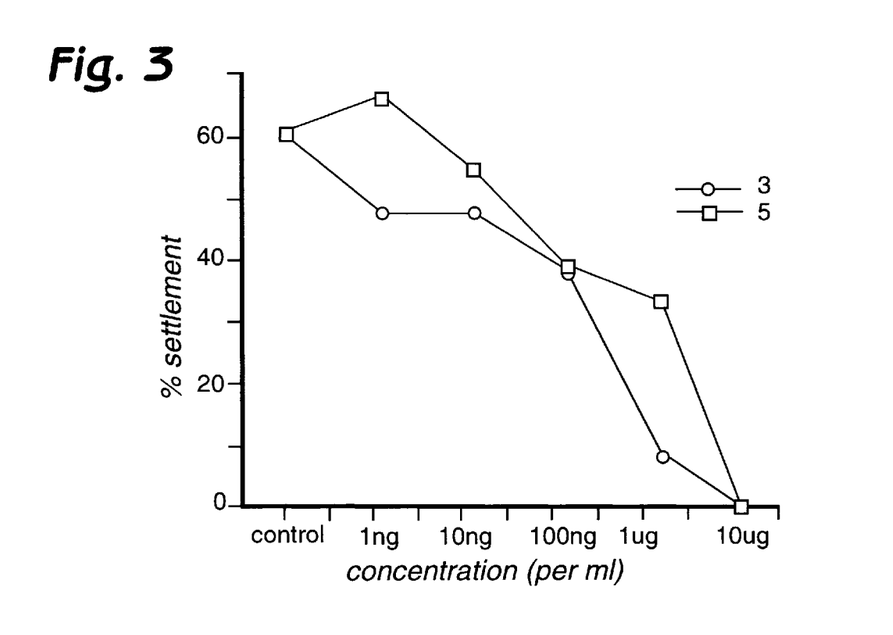
FIG. 3 shows the effects of the metabolites dissolved in water in cyprid settlement for compounds 3 and 5.

EC50 values for these compounds, based on the data in FIGS. 2 and 3, are presented in Table 2. Two of the compounds had EC50 values <100 ng/ml, and 5 of the compounds had EC50's significantly less than that of $CuSO_4$. Following the reduction in the use of tin-based compounds, copper (Cu) is now the main active ingredient in antifouling paints.

TABLE 2

| metabolite | $EC_{50}$ (μg/ml) + 95% conf. int. |
|---|---|
| 1 | 0.02(0.01–0.04) |
| 2 | 0.02(0.00–0.04) |
| 3 | 0.06(0.03–0.11) |
| 4 | 0.32(0.17–0.60) |

TABLE 2-continued

| metabolite | EC$_{50}$ ($\mu$g/ml) + 95% conf. int. |
|---|---|
| 5 | 0.51(0.29–0.89) |
| CuSO$_4$ | 0.40(0.25–0.77) |

These compounds were also active against settlement when applied to the surface of the dishes (FIG. 4), though their activity was perhaps somewhat less than when dissolved in the water.

The effects of surface coatings of metabolites 1–4 against the settlement of barnacle cyprid larvae are shown in FIG. 4. All compounds completely inhibited settlement of cyprids at 25 $\mu$g/cm2. Compounds 3 and 4 were as previously described the most inhibitory completely deterring settlement at 2.5 $\mu$g/cm2 and significantly deterring settlement at 250 ng/cm2.

Algal Spore Assays

The effects of surface coatings of metabolites 1–4 coated against the settlement of and germination of algal spores are shown in FIG. 5. All compounds completely inhibited settlement of algal spores at 25 $\mu$g/cm$^2$. Compounds 2 and 4 significantly deterred settlement and germination at a concentration of 250 ng respectively, while the most deterrent metabolite, compound 3, inhibited settlement and germination by >90% at a concentration of 25 ng/cm$^2$.

Inhibition of Bacterial Growth

Figure 6:
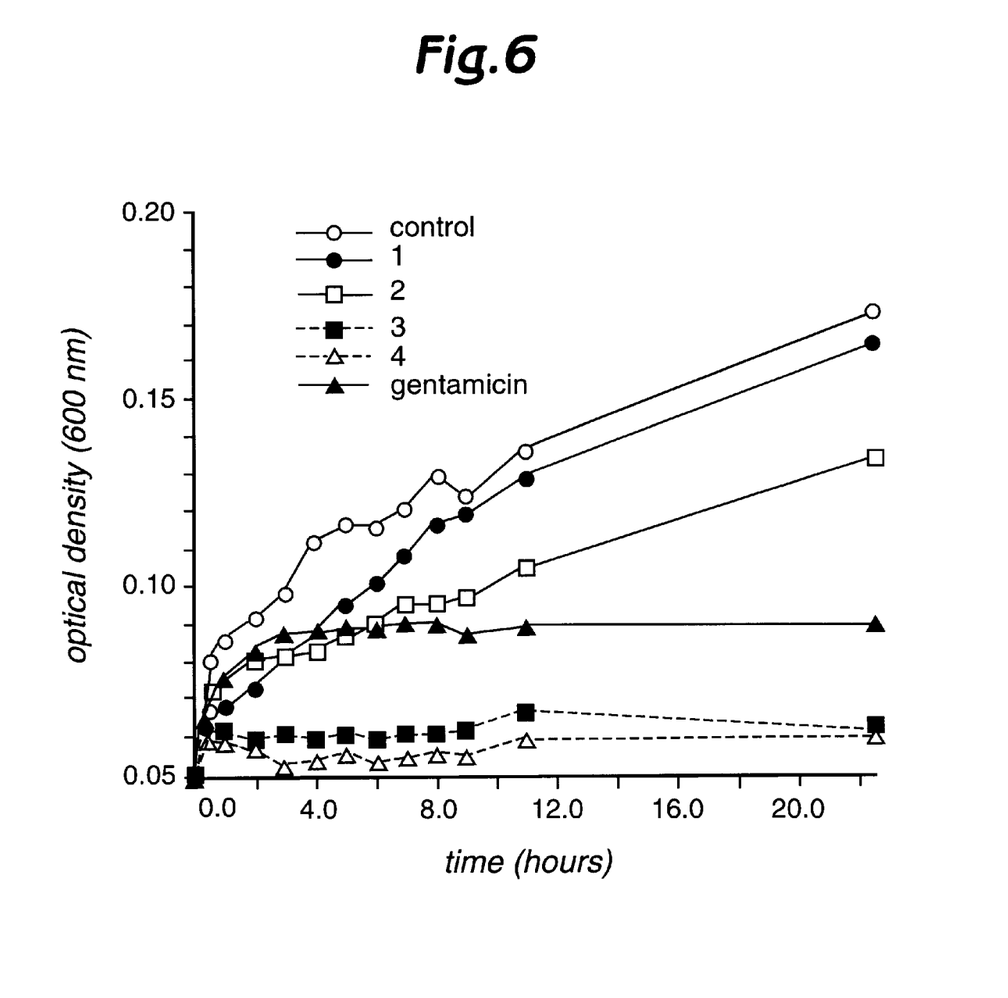
FIG. 6 is a plot of optical density versus time demonstrating inhibition of the growth of the marine bacterium SW8 by Delisea metabolites.

Delisea metabolites significantly inhibited the growth of the marine bacterium SW8 at all times analysed, i.e. at 4, 11.5 and 25 hours (FIG. 6, Table 3). At none of these times was there any significant difference between ethyl acetate and media controls (one factor ANOVA, p <0.05) and only ethyl acetate controls were used in further analyses. The effect on bacterial growth differed significantly among metabolites and between concentrations (FIG. 6, Table 3). Compounds 3 and 4 were the most active, completely inhibiting growth at a concentration of 10 $\mu$g/ml (FIG. 6, Table 3), and still causing some inhibition of growth at 10 ng/ml (Table 3). Compounds 3 and 4 were significantly more inhibitory than the antibiotic gentamicin.

TABLE 3

| concentration | Compounds in order of increasing activity | | | | | |
|---|---|---|---|---|---|---|
| A) 4 hours | | | | | | |
| 10 $\mu$g/mL | c | 1 | gent | 2 | 3 | 4 |
| 1.0 $\mu$g/mL | c | gent | 2 | 1 | 4 | 3 |
| 100 ng/mL | gent | 4 | c | 2 | 3 | 1 |
| 10 ng/mL | gent | c | 4 | 2 | 1 | 3 |
| B) 11.5 hours | | | | | | |
| 10 $\mu$g/mL | c | 1 | 2 | gent | 3 | 4 |
| 1.0 $\mu$g/mL | c | gent | 1 | 2 | 3 | 4 |
| 100 ng/mL | gent | 4 | 2 | c | 1 | 3 |
| 10 ng/mL | gent | c | 2 | 4 | 1 | 3 |
| 10 $\mu$g/mL | c | 1 | 2 | gent | 3 | 4 |
| 1.0 $\mu$g/mL | 2 | c | 1 | 3 | 4 | gent |
| 100 ng/mL | gent | 4 | 3 | 2 | c | 1 |
| 10 ng/mL | gent | 4 | 1 | c | 3 | 2 |

Figure 7:
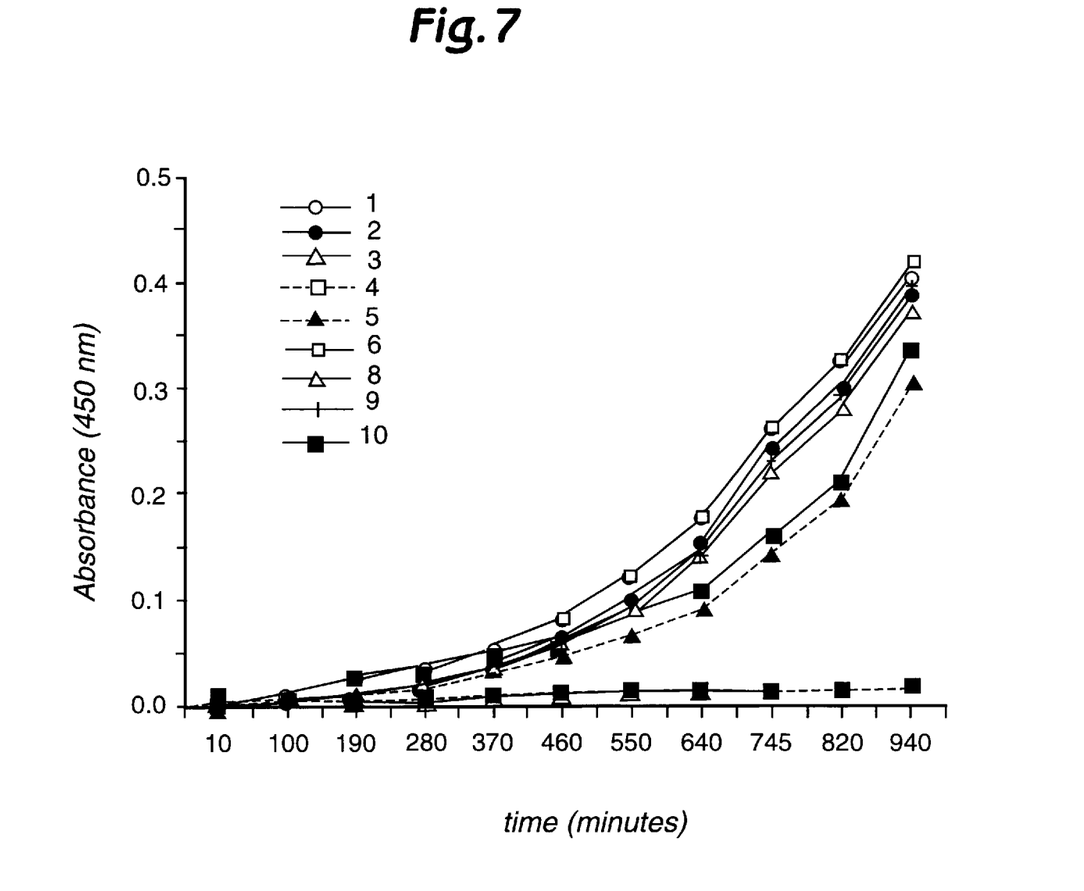
FIG. 7 is a plot of absorbance versus time demonstrating the results of tests using *Vibrio fischeri*.

The results of the tests using *Vibrio fischeri* are shown in FIG. 7. As with the inhibition of SW8 compounds 3 and 4 were most inhibitory completely deterring growth over the duration of the experiment. Compounds 5 and 10 were also significantly inhibitory, however, inhibition of growth by these compounds decreased with time and they were not significantly different from the control after 940 minutes.

Inhibition of the Settlement of Bryozoan Larvae

Figure 8:
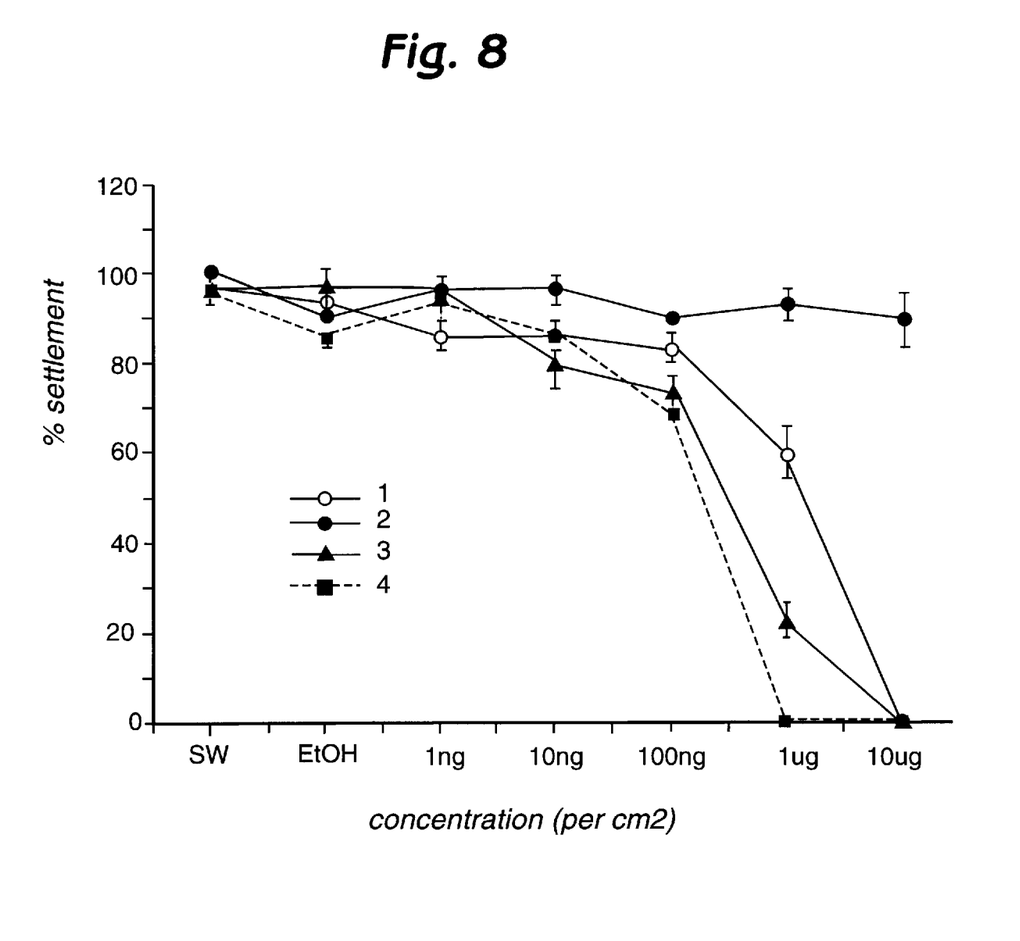
FIG. 8 is a plot of percentage settlement versus concentration demonstrating the results of inhibition of settlement of byrozoan larvae.

The results for the inhibition of settlement of byrozoan larvae are shown in FIG. 8 Compounds 1, 3 and 4 significantly completely inhibited the settlement of *Buaula neretina* larvae at 10 $\mu$g/cm$^2$ while the most active compound, 4, completely deterred settlement at a concentration of 1 $\mu$g/cm$^2$.

Field Assessment of Activities

Because of the variable nature of the Delisea metabolites against different fouling organisms, and because the variation in chemical structure among the metabolites is likely to significantly affect how they are incorporated into polymer coatings, extensive field testing has not yet been done. Initial field tests, in which crude extracts of Delisea were incorporated into resin (UCAR solution vinyl resin VYHH) and placed in the field for 3 months, indicated significant inhibition of fouling relative to control resins lacking added metabolites.

Discussion and Conclusions

Two major points emerge from the tests of Delisea metabolites done to date:

Firstly, the compounds are very active, at low concentrations, against representatives from four major groups of fouling organisms. For comparison, EC$_{50}$'s of previously reported natural products (and copper) in cyprid assays (see literature cited in Background Art), are, with one exception (the "renillafoulines", Rittschof et al. 1994) typically in the range of 100's of ng/ml to 1 $\mu$g/ml. EC$_{50}$'s of three of the Delisea compounds fall at the lower end of this range, and EC$_{50}$'s of two of the compounds fall well below it.

Thus these compounds are as or more active then almost all other previously described natural antifoulants. Their activity also compares favourably to that of tributyl tin, the antifoulant of choice for the past 15 years.

Moreover, the activity of the compounds is broad spectrum. This is a significant advantage over most previously described natural antifoulants, which have tended to focus on the activity of the compounds against barnacle larvae, or at most invertebrates and bacteria (Holmstrom and Kjelleberg 1994). Clearly any antifouling coating must work against the range of fouling organisms which occur in the field, and thus the Delisea metabolites broad spectrum activities are very important. Their strong activities against algal spores is a major benefit in and of itself, since algae have often proven to be the most difficult foulers to control.

The second major point to emerge is that the structural variation that exists among the Delisea metabolites is very important in terms of the compounds' effects on fouling organisms. Tests against any one fouling organism indicate significant variation in the effects of different compounds (e.g. FIGS. 2–8), and the relative effects of each compound against different organisms is not the same. For example, the most effective compound against barnacle larvae is 1 and 2; against bacteria 3 and 4, and; against algal spores compound 3.

This variation in the effects of the compounds against different fouling organisms has several major implications for using these compounds in the development of antifouling paints. Firstly, a broadly effective paint, or other film forming composition, is likely to contain a mixture of these compounds, each of which will be most effective against a certain suite of fouling organisms. Secondly, the particular polymer matrix e.g., the coating base to be used, will have to be chosen with particular care in order to maximise the efficiency of the different compounds within the paint. Compounds 1–4 (and the additional metabolites) vary in their chemical properties as well as their biological activities. Thus some compounds will incorporate easily into a given polymer, but not into others.

Finally, of crucial importance to any commercial antifouling product is the ability to produce it in large quantities. Syntheses of several of the Delisea compounds, and closely related structures, have been published (Jefford et al. 1988, 1989). The syntheses are relatively short and of high yield, and indicate that industrial scale production of the compounds is certainly possible.

REFERENCE

Dalley R (1989) Legislation affecting tributyltin antifoulings. Biofouling 1: 363–366 de Nys R, Coll J C, Bowden BF (1992) *Delisea pulchra* (cf. *fimbriata*) revisited. The structural determination of two new metabolites from the red alga Delisea pulchra. Aus. J. Chem. 45: 1625–1632 de Nys R, Wright A D, Konig G M, Sticher O (1993) New halogenated furanones from the marine alga *Delisea pulchra* (cf. *fimbriata*). Tetrahedron 49: 11213–11220

Fletcher R L (1989) A bioassay technique using the marine fouling green alga Enteromornha. Int. Biodeterioration 25: 407–422

Gerhardt D J. Rittschof D, Mayo S W (1988) Chemical ecology and the search for antifoulants. J Chem Ecol 14: 1903–1915

Hamilton M A, Russo, R C, Thurston R V, (1977) Trimmed Spearmann-Karber method for estimating median lethal concentrations in toxicity bioassays. Environ. Sci. Technol. 11(7): 714–719

Holmstrom C, Rittschof D, Kjelleberg S (1992) Inhibition of settlement by larvae of *Balanus amnhitrite* and *Ciona intestinals* by a surface-colonizing marine bacterium. Appl Environ Microbial 58: 2111–2115

Holmstrom C and Kjelleberg, S (1994) The effect of external biological factors on settlement of marine invertebrate larvae and new antifouling technology. Biofouling: in press.

Jefford,. C W, Jaggi, D, Boulcouvalas. J (1988) J. Chem, Soc., Chem. Commun. :1595

Jefford, C.W. Jaggi, D, Sledeski, A W, Boukouvalas. J (1989) Stud. Nat. Prod. Chem. 3: 157

Kazlauskas R, Murphy P T, Quinn R J. Wells R J (1977) A new class of halogenated lactones from the red alga *Delisea fimbriata* (Bonnemaisoniaceae). Tet. Lett.1: 37–40

Keifer, P A, Rinehart, K L Hooper I. R. (1986) Renillafoulins, antifouling diterpenes from the sea pansy *Renilla reniformis* (Octocorallia) J. Org. Chem. 51: 4450–4454

Leslie G L, Schmeider R P, Fane A G, Marshall K C, Fell C J D (1993) Fouling of a microfiltration membrane by two gramnegative bacteria. Colloids and Surfaces A: Physicochemical and Engineering Aspects 73: 165–178

Maki J S, Rittschof D, Schmidt A R, Snyder AG, Mitchell R (1989) Factors controlling attachment of Bryozoan larvae. A comparison of bacterial films and unfilmed surfaces. Biol Bull 177: 295–302

Mary A S, Mary V S R., Rittschof D, Nagabhushanam R (1993) Bacterial-barnacle interaction: potential using juncellins and antibiotics to alter structure of bacterial communities. J Chem Ecol 19: 2155–2167

Neu T R, Marshall K C (1991) Microbial "footprints"—new approach to adhesive polymers. Biofouling 3: 101–112

Rittschof D, Hooper I R, Bransconi E S, Costlow J D (1985) Inhibition of barnacle settlement and behaviour by natural products from which corals, *Lentogoraia viraulata* (Lamarclc, 1985) J Chem Ecol-11: 551–564

Rittschof D, Clare, A S, Gerhardt, D J, Mary A, Bonaventura J (1993) Barnacle in vitro assays for biologically active substances: toxicity and settlement inhibition assays using mass cultured *Balanus amphitrite* amphitrite Darwin. Biofouling 6:

Schneider R P, Marshall K C (1994) Retention of the gram-negative marine bacterium SW8 on surfaces-effects of microbial physiology, substratum nature and conditioning films. Colloids and Surfaces B: Biointerfaces in press:

Standing J D, Hooper I R, Costlow J D (1984) Inhibition and induction of barnacle settlement by natural products present in octocorals. J Chem Ecol 10: 823–824

Targett N M, Bishop S S, McConnell O J, Yoder H A (1983) Antifouling agents against the benthic marine diatom, *Navicula salinicola*. J Chem Ecol 9: 817–829

Todd J S, Zimmerman R C, Crews P., Randall S A (1993) The antifouling activity of natural and synthetic phenolic acid sulfate esters. Phytochemistry 34, sep: 401–404.

We claim:

1. An antifouling composition comprising an effective amount of a furanone of the formula:

wherein $R_1$ is hydrogen, a hyroxyl group, an alkyl group containing from 1 to 10 carbon atoms, an ether group containing from 1 to 10 carbon atoms, an ester group containing from 1 to 10 carbon atoms or a halogenated alkene containing from 1 to 10 carbon atoms, $R_2$ is hydrogen or bromine, $R_3$ is halogen, and $R_4$ is hydrogen or bromine; and a suitable carrier therefor.

2. An antifouling composition as claimed in claim 1 in which $R_1$ is hydrogen, hydroxyl, an ester or an ether group, and $R_4$ is bromine.

3. An antifouling composition as claimed in claim 1 in which $R_1$ is selected from the group consisting of hydrogen, hydroxy and acetoxy.

4. An antifouling composition as claimed in claim 1 in which $R_3$ is chlorine, bromine or iodine.

5. An antifouling composition as claimed in claim 1 in which $R_1$ is an acetyl group.

6. An antifouling composition as claimed in claim 1 in which $R_1$ is a hydroxy group and $R_2$ and $R_3$ are each bromine.

7. An antifouling composition as claimed in claim 1 containing two or more of the furanones of formula I.

8. An antifouling composition as claimed in claim 1 in which the carrier is a paint or other dryable film-forming composition.

9. A process for the prevention of marine fouling of an object comprising:

applying to at least a part of the object a coating of the composition according to claim 1, incorporating in a least that part of the object itself such a composition, and immersing at least that part of the object into water.

* * * * *